(12) United States Patent
Allam et al.

(10) Patent No.: US 8,357,507 B2
(45) Date of Patent: Jan. 22, 2013

(54) WATER SOLUBLE FLUORESCENT QUANTUM CARBON DOTS

(75) Inventors: Afreen Allam, Raleigh, NC (US); Sabyasachi Sarkar, Jamtara (IN)

(73) Assignee: Cromoz Inc., Raleigh, NC (US)

( * ) Notice: Subject to any disclaimer, the term of this patent is extended or adjusted under 35 U.S.C. 154(b) by 354 days.

(21) Appl. No.: 12/719,791

(22) Filed: Mar. 8, 2010

(65) Prior Publication Data
US 2011/0217721 A1 Sep. 8, 2011

(51) Int. Cl.
*C12Q 1/02* (2006.01)
(52) U.S. Cl. .......................... 435/29; 977/734
(58) Field of Classification Search .................. None
See application file for complete search history.

(56) References Cited

U.S. PATENT DOCUMENTS

| | | | |
|---|---|---|---|
| 7,235,361 B2 * | 6/2007 | Bawendi et al. | 506/17 |
| 7,767,185 B2 * | 8/2010 | Ishida et al. | 423/447.1 |
| 2008/0213367 A1 | 9/2008 | Sarkar et al. | |

OTHER PUBLICATIONS

Yang et al. Carbon dots as nontoxic and high-performance fluorescence imaging agents. J. Phys. Chem. (2009) vol. 113, pp. 18110-18114.*
Larson et al. Water-soluble quantum dots for multiphoton fluorescence imaging in vivo. Science (2003) vol. 300, pp. 1434-1436.*
Ya-Ping Sun et al., Carbon Dots for Multiphoton Bioimaging, J. American Chemical Society, 2006, 128 7756-7757.
Quantum Dot, Wikipedia, the free encyclopedia, http://en.wikipedia.org/wiki/Quantum_dot, (2010).
Yang et al. (Journal of the American Chemical Society (2006) 128:7756-7757).

* cited by examiner

*Primary Examiner* — Kenneth R. Horlick
*Assistant Examiner* — David Thomas
(74) *Attorney, Agent, or Firm* — James G. Passé; Passé Intellectual Property, LLC (57) ABSTRACT

The present invention relates to the water soluble self fluorescent quantum carbon dots (C-dots). These C-dots are isolated from carbon soot in one embodiment a wax soot solvent washed and isolated from other larger material by filtration such as by membrane filtration. The C-dots can be varied in their color by change of their size and by the amount of oxidative groups' position on each C-dot.

13 Claims, 8 Drawing Sheets

Carbon Nano Dot Uptake in Cancer Cells

Ovary Cancer cell line, SKOV-3
Incubation Time    24 hour

WATER SOLUBLE FLUORESCENT QUANTUM CARBON DOTS

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates compositions and methods for producing water soluble fluorescent quantum carbon dots (C-dots). In particular, the present invention relates to the production of water soluble C-dots using a carbon nano tube production method followed by filtration and oxidation. The C-dots are self fluorescing and can be modified to produce a range of color fluorescences.

2. Description of Related Art

Quantum dots are the subject of much research and investigation using a wide variety of materials. Several different materials are being used in an attempt to convert them into a quantum confined type dot. Quantum sized carbon dots are roughly defined as nano sized carbon dots with a diameter in the range of 2 to 10 nanometers and comprised of spherical form of very small size but larger than fullerene made out of graphene sheets of very small size. Previously C-dots have been produced by laser beam ablation of a carbon target. The carbon target is prepared by hot-pressing a mixture of graphite powder and cement, followed by a stepwise baking, curing and then annealing in an argon flow A laser. The laser is used for the ablation during which the carbon target is in a flow of argon gas carrying water vapor (usually through a water bubbler) at 900° C. and 75 kPa. However, this technique chiefly produces nano scale carbon particles to be treated further to produce a C-dot suspension and further surface passivation by attaching organic molecules. None of these types of C-dots are capable of self fluorescing.

These known materials are produced with techniques that are not only difficult to consistently repeat but do not lend themselves to practical mass producing. In addition starting material synthesis is difficult and the entire process is expensive because of the materials and temperatures needed. To date a practical production of C-dots has not been discovered.

Currently, C-dots are not self fluorescent but are caused to fluoresce by addition of a coating, by surface modification or by addition of a fluorescent molecule, such as a bacterial produced green fluorescent protein. This approach adds extra costs as well as complexity and is limited in the color change achievable with each technique.

It was reported (Ya-Ping Sun et al, J. American Chemical Society, 2006, 128, 7756-7757) that quantum-sized carbon dots are soluble in water and show bright and colorful photoluminescence only because of passivation of these carbon nano particles by organic molecules. Therefore, conventionally prepared carbon dots are not applicable to practical use as self fluorescent material.

Carbon nanotubes have been isolated from carbon soot by solvent washing. That production is described in U.S. patent application Ser. No. 11/680,888 filed Mar. 1, 2007 and incorporated herein by reference in its entirety. There is no reference to the existence or isolation of quantum materials of any kind.

BRIEF SUMMARY OF THE INVENTION

The present invention relates to the discovery that water soluble carbon dots can be isolated from carbon soot and if carboxylated on the surface to a sufficient degree will be water soluble and will self fluoresce. In addition the color of florescence will change based on the change in the size of these water soluble carbon dots.

Accordingly, in one embodiment of the present invention, there is disclosed a water soluble self fluorescing quantum carbon dot comprising a carbon dot isolated from carbon soot and treated to produce hydrophilic carboxylic acid groups on the surface of the carbon dot sufficient to cause fluorescence.

In yet another embodiment of the present invention, there is disclosed a method of producing a fluorescent quantum carbon dot comprising
  a. heating a hydrocarbon wax to a temperature of between about 500 degree C. and 800 degree C. under conditions sufficient to produce carbon soot;
  b. collecting and purifying the soot to isolate quantum carbon dots;
  c. oxidatively treating the quantum carbon dots to remove amorphous carbon and produce hydrophilic carboxylic acid groups on the surface of the dots sufficient to cause the dots to fluoresce.

In yet another embodiment of the invention, there is a method of tagging a molecule or biological system comprising associating a water soluble fluorescing quantum carbon dot with the molecule or biological system.

DETAILED DESCRIPTION OF THE INVENTION

While this invention is susceptible to embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "water soluble" has its typical meaning. That is the physical property describing the ability of the C-dots of the present invention to dissolve in the solvent water. Differing compositions dissolve at differing rates but in general the dissolution rate of the C-dots of the invention is 30 mg in 1 ml of water.

"Fluorescing", as used herein, refers to the carbon dots self capability to produce a luminescence upon release of energy after being expose to a photon source of a given wavelength. Typically fluorescence occurs at a different wavelength than the excitation wavelength of photons used to create the fluorescence. As described herein, the amount of carboxylic acid groups on the varying size of the surface of each C-dot determines the color at which the C-dot can fluoresce. See the examples and figures for specific embodiments. Armed with this discovery one skilled in the art can easily separate the C-dots based on size to produce a given color fluorescence on a consistent basis.

A "quantum carbon dot" or a C-dot as used herein is a carbon nano particle, generally of a graphene framework and of a generally spherical structure. C-dots of the invention are in the nano range of about 2 to 20 nanometers (nm) in diameter while many are in the 2 to 7 and 7 to 20 nm size. The hydrophilic carboxylic acid groups on the surface of the carbon dot not only contribute to the water solubility of the C-dot, it also allows the C-dot to be able to self fluoresce upon exposure to a light (photon) source. Once again the visible wavelength of the fluorescence will vary with the amount of oxidative carboxylic sites on each C-dot and the size of the carbon dot. The size of the C-dot can be controlled by filtration or other size or weight separating techniques used for nano sized particles. Thus varying the size of C-dots the emission wave lengths are varied resulting in display of different color images.

As used herein, the term "soot" refers to the black, impure carbon resulting from the incomplete combustion of a hydrocarbon. It is also described as the product of the gas-phase combustion process but is commonly extended to include the residual pyrolyzed fuel particles such as cenospheres, charred wood, petroleum coke, etc. that may become airborne during pyrolysis and which are more properly identified as cokes or chars. In one embodiment of the present invention the soot is produced from a hydrocarbon wax.

As used herein the term "hydrocarbon wax" refers to those hydrocarbons having properties similar to beeswax namely malleable at normal ambient temperature, a melting point above about 45 degrees C., a low viscosity when melted, insoluble in water and hydrophobic. Waxes can be natural origin or artificial. Chemically a way may be an ester of ethylene glycol and two fatty acids. Several different categories of hydrocarbon waxes are known for example animal waxes, insect waxes, mineral waxes, petroleum waxes and synthetic waxes. In one embodiment the wax can be selected but not limited to beeswax, carnauba wax, castor wax, jojoba wax, rice bran wax, ceresin waxes, ozocerite wax, paraffin wax, microcrystalline wax, polyethylene wax and the like.

As used herein the phrase "conditions sufficient to produce carbon soot" refers to the burning of the hydrocarbon such as a hydrocarbon wax under conditions of oxygen supply sufficient to produce soot. Specific examples of carbonaceous matter may include but are not limited to wax; including waxes of mineral origin with the melting point below 80 degrees C. and also from bee-hives and the like. It can also extend to use of cellulose plant material pure cellulose, wood, wool or charcoal. Soot in general results from the incomplete combustion of the hydrocarbon in the wax. Typically this means that the flame is deprived of sufficient oxygen to combust entirely. It also is useful that convection type conditions exist during the combustion effort such as would exist with an open flame. For example, the burning of a bees wax candle creates a convection or uplifting draft which carries the soot away from the flame and aids in the prevention of complete combustion. Typically the flame used to produce soot is at a temperature of between about 500 and 800 degrees C. usually as an open flame however other sources of heat that produce soot are well known. The result of this production is the production of amorphous carbon and of multi-walled concentric carbon nano tubes of the type consistent with the Russian Doll model. In addition it has been discovered that C-dots of the present invention can also be isolated from this mixture of combustion products. These dots are very stable and benign to biological cells and can fluoresce for a longer time span before biodegradation than naturally occurring fluorescent proteins such as GFPs (Green Fluorescent Proteins).

For example, a fire is applied to a central thread to glow in the case of wax or oil as the source of carbon and the soot so produced at the top of the flame is collected on the surface of a glass plate (or metal sheet collector) whereby the carbon material comprising carbon nano tubes and carbon nano particles are deposited. In the case of solid carbon source like wood, it is fired and allowed to glow and the soot generated at the top of the flame of burning wood is collected similarly as stated above.

As used herein the phrase "purifying the soot" refers to a solvent washing for example with an organic solvent, of the soot to remove organic byproduct soluble in organic solvent. Suitable solvents are used in separating the amorphous carbon from the nano tubes and C-dots is by either differences in density, weight or the like of the products by flotation method. Examples of specific solvents for use in the invention include, but are not limited to, nitric acid of different dilution and aqueous salt solution of varied strength of the salt. In order to separate the C-dots from the nanotubes produced a simple filtration method can be utilized to take advantage of the vastly differing size of the C-dots versus the nano tubes. For example, a membrane with a suitable pore size from about 0.1 micrometer to about 0.45 micrometer (in one embodiment a 0.2 micrometer filter pore size) could be used by one skilled in the art using normal membrane filtration techniques. Other methods of separation could include gel and other chromatographic techniques. In the end the collected c-dots are usually in the range of about 2 nm to about 7 nm although larger and smaller can be produced with this method.

As used herein "oxidatively treating" refers to treatment of the isolated C-dots with an oxidizing agent such that a portion of the C-dots being reactive is exposed to an oxidizing agent to produce carboxylic acid groups attached at that point. The point of attachment can be any portion on the outer surface of the C-dot. Oxidizing agents suitable for use in the invention include but are not limited to nitric acid, per acids, ammonium cerium nitrate, nitrogen dioxide, chlorine oxide. Oxidizing agents can be mixed together as well so in one embodiment nitric acid could be combined with sulfuric acid, sodium meta bisulfate or a per acid. The concentration and time of exposure of the oxidizing agent to the nano tube depends on the temperature, the oxidizing agent selected, the time of exposure, the amount of functionalization desired and the like but is well within the skill in the art in view of the disclosure herein in order to acquire the fluorescence and of what color.

As used herein, the term "carboxylic acid group" refers in general to the chemistry of oxidizing a hydrocarbon C-dot tube as follows: On standing the purified soot under concentrated nitric acid for prolong period (24-48 hours) resulted in carboxylation of the surface of the C-dot. The nitric acid is evaporated, the residue is then sonicated in water followed by filtration using 0.85 micrometer size filter. The filtrate is then evaporated to dryness to yield C-Dot which is separated from larger CNTs and the residual amorphous carbon. The nitration on carbon centers results in nitro group. This nitro group changes to isonitro (isomerization) followed by its hydrolysis to hydroxo, which on further oxidation results in a carboxylic acid group. The yield of the soluble part varies with the time of oxidation. This ranges from 20 to 40 percent of the starting C-dot's. The oxidation can be carried out by concentrated nitric acid or by a mixture of nitric acid/sulfuric acid or by sulfuric acid and potassium hydrogen sulfate or by persulfate and sulfuric acid or by hydrogen peroxide and sulfuric acid mixture or other per acid salts like perborate or perhalate and acid. Besides acids, nitrogen dioxide chlorine dioxide can be used as oxidant to introduce labile functional groups which under hydrolysis and finally under acid treatment led to form relatively more stable carboxylate acid groups.

As used herein, "bonded to a desired molecule" refers to forming a bond with another molecule such that the molecules presence can be detected by the presence of the fluorescent tag. Green Fluorescent Proteins or GFPs and the like have been used for years as such tags and likewise the C-dots of the present invention can be used. Such is within the skill in the art, knowing that these compounds fluoresce. The C-dots can be attached by Vanderwaal forces, hydrogen bonding covalent bonding or the like by known methods. In addition "attached to a molecule" can also include being absorbed, carried by, ingested or the like by a biological organism. This can be by osmotic methods, absorption, ingestion and the like. In these cases, the C-dot need not actually be attached but in this case bonded would refer to associated with a biological organism such that it acts as a tag.

The present invention provides water soluble fluorescent carbon nano particles as quantum sized carbon dots which are excellent in displaying self fluorescence and may be used with continuous variation of the excitation wavelength from about 400 to 650 nm to display emission in varied wavelength controlled by the structure and shape of the nano-carbon particle-dots. The present invention also discloses a novel method that enables easy industrial production of such C-dots in high yield and high mass-productivity. These C-dots can be encapsulated, bonded, associated with or the like with a carrier, biological molecule or living entity for use in delivering or tagging and imaging the site.

These C-dots have the advantage that by varying the nano size (for example by varying the diameter) and the distribution and amount of carboxylic acid groups on the surface of the C-dots provide, 1) tunability with excitation energy to fluoresce with varied emission lines; 2) vary their solubility; 3) vary their ability to associate with and transport soluble chemicals, living organisms and biomolecules and 3) vary their ability to hold those chemicals, biomolecules and living organisms. 4) These are more stable than conventional GFP and therefore stay in the probe site for longer time especially for bio-imaging of cancer cells and alike and these are benign to biological cell. The particular method of producing the dots allows for production in high purity, high yield and high mass productivity.

EXAMPLES

Example 1

Production of C-dot Containing Soot.

A bee's wax candle was lit and allowed to burn via its central cotton wick under normal open air conditions. Carbon soot is collected on a glass reflector plate, is fixed over the candle and repositioned as needed during the burning process. The temperature during this burning process was recorded and was about 600 degrees Centigrade during the entire process. The collected soot was then washed repeatedly with toluene, acetonitrile and ethanol by soxhlet method to free the soot from any unburnt hydrocarbon or fullerenes and then dried. The result was a mixture of nano tubes and C-dots.

Example 2

Preparing Water Soluble of C-dots and CNT Nanotubes.

The C-dots from example 1 are treated with concentrated nitric acid and the mixture is allowed to stand for 24-48 hours under ambient room temperature and atmospheric pressure till the entire mass is dried. The mass was washed with cold distilled water and the black residue was suspended with distilled water and sonicated to dissolve the water soluble C-dots and water soluble CNTs. The mixture was filtered through bulk membrane filtration to remove most CNTs from C-dots. These C-dots were collected from the evaporated filtrate.

Example 3

Separating after Soluble C-dots that Fluoresce.

The C-dots from example 2 were then treated with water and sonicated to dissolve and passed through membranes of sizes 0.45, 0.2 and 0.01 micrometer respectively. The separated filtrates were collected and evaporated to dryness under vacuum desiccators to yield C-dots of different sizes functionalized by carboxylic acid groups on the surface. The average yield of C-dots is from 400 mg to 900 mg of water soluble carboxylated mixture of C-dot and water soluble CNTs isolated from burning 50 grams of bee's wax. The resulting C-dots can fluoresce in a wavelength range of between 400 to 650 nm. The figures which follow display the analysis of the produced C-dots.

Figure 1:
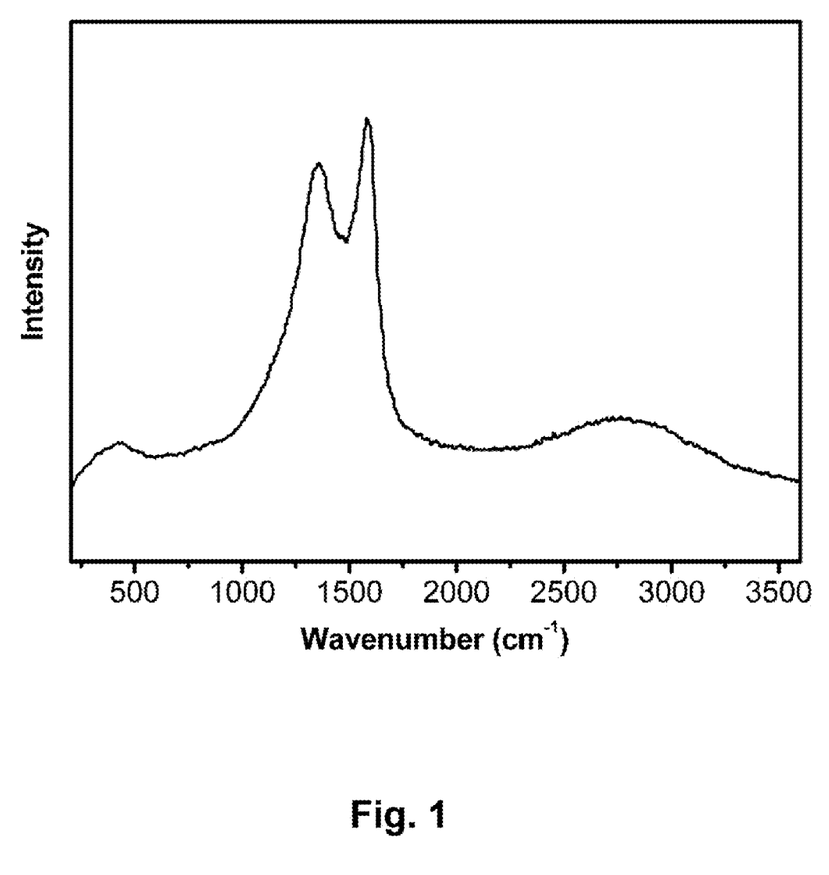
FIG. 1 is a Raman spectrum of C-dots of the present invention.

FIG. 1 shows a graph of the water soluble fluorescent carbon nano particles as quantum sized carbon dots (passed 0.20 micrometer membrane) showing D and G band with mixing of overtones around 2700 $cm^{-1}$ in Raman Spectrum.

Figure 2:
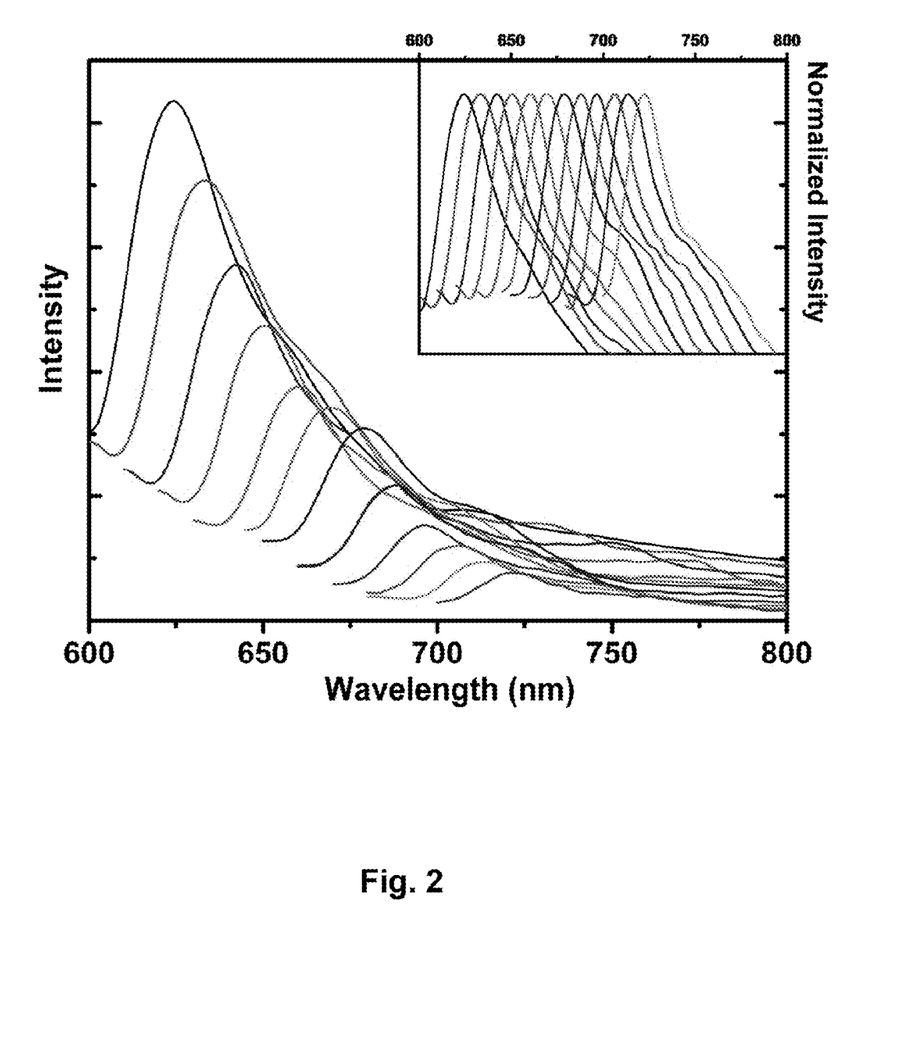
FIG. 2 is luminescence emission spectra of several different C-dots of the present invention.

FIG. 2 shows the luminescence emission spectra (with progressively longer excitation wavelengths from 450 nm on the left in 15 nm increment) of water soluble fluorescent carbon nano particles (GNPs) as quantum sized carbon dots in an aqueous solution. The emission spectral intensities are normalized to quantum yields (normalized to spectral peaks in the inset).

Figure 3A:
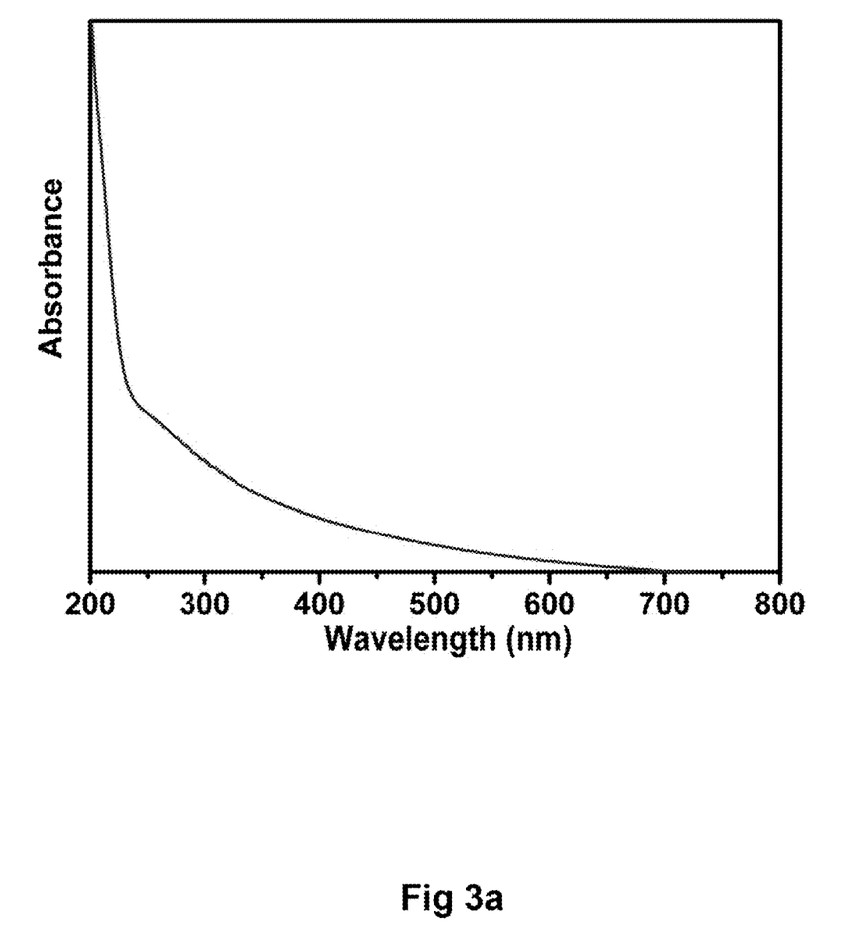
FIG. 3a is a UV visible spectrum of C-dots in water.
Figure 3B:
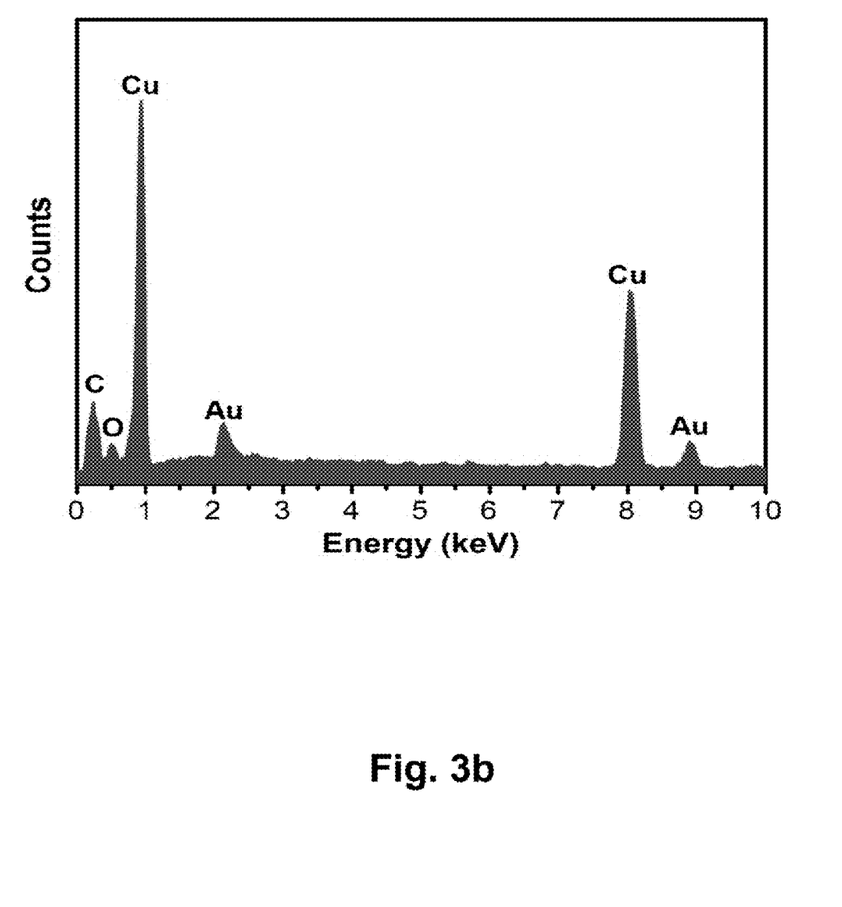
FIG. 3b is an EDX spectrum of C-dots of the present invention.

FIG. 3a shows those c-dots fluorescence as UV visible spectrum as the C-dots are in an aqueous solution. FIG. 3b depicts the EDX spectra of the C-dots.

Figure 4A:
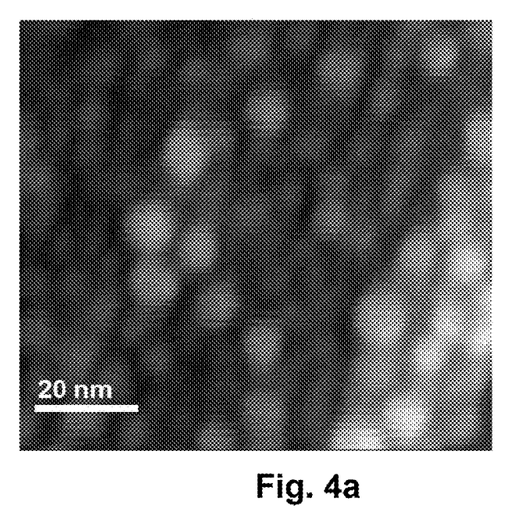
FIG. 4a is an SEM image of C-dots of the present invention.
Figure 4B:
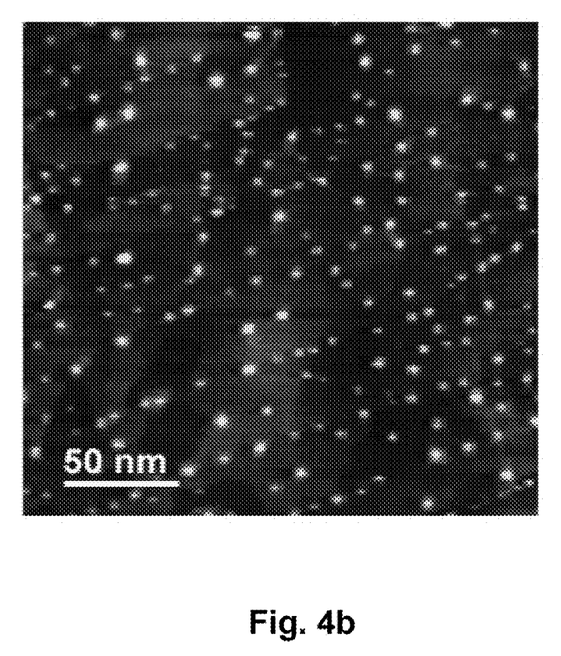
FIG. 4b is an AFM image of C-dots of the present invention.
Figure 5:
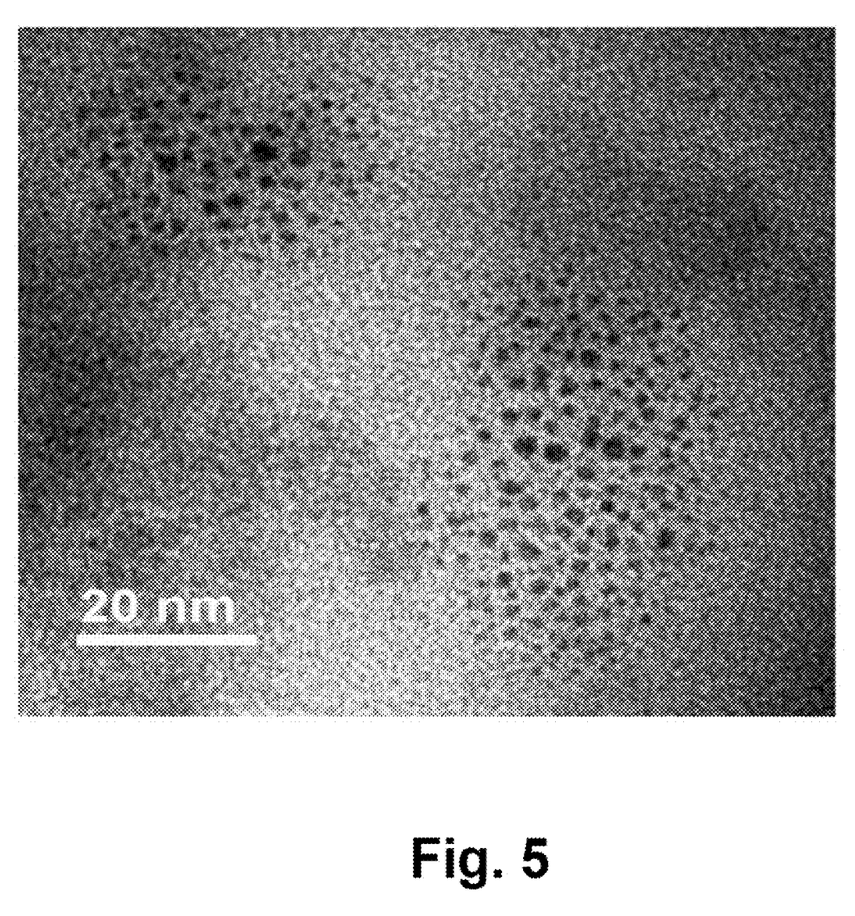
FIG. 5 is a TEM image of C-dots of the present invention.

FIGS. 4a, 4b and 5 depict images of C-dots taken by SEM, AFM and TEM respectively showing the consistency of size and shape of the C-dots with this method.

Figure 6:
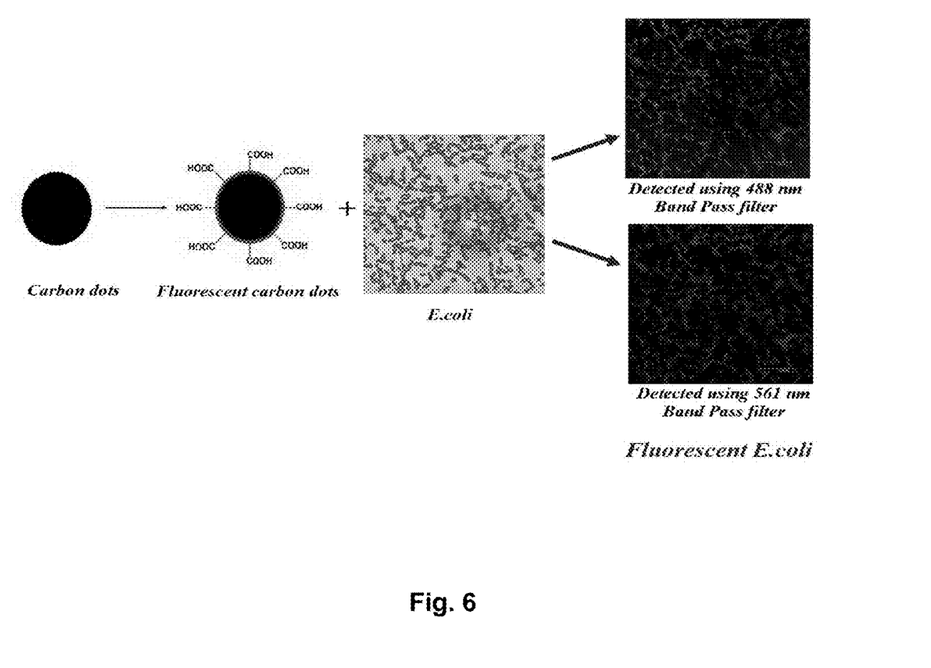
FIG. 6 is confocal microscopy images of *E. coli* tagged with C-dots of the present invention.

FIG. 6 shows confocal microscopy photo images of fluorescent *E. coli* tagged with the C-dots. The C-dots were added in the growth medium of *E. coli* wherein C-dots pass through the membranes of E-coli without affecting the cell cycle. The incorporation of these can be manifested easily by imaging the C-dot treated E-coli which showed fluorescence using different light filters.

Figure 7:
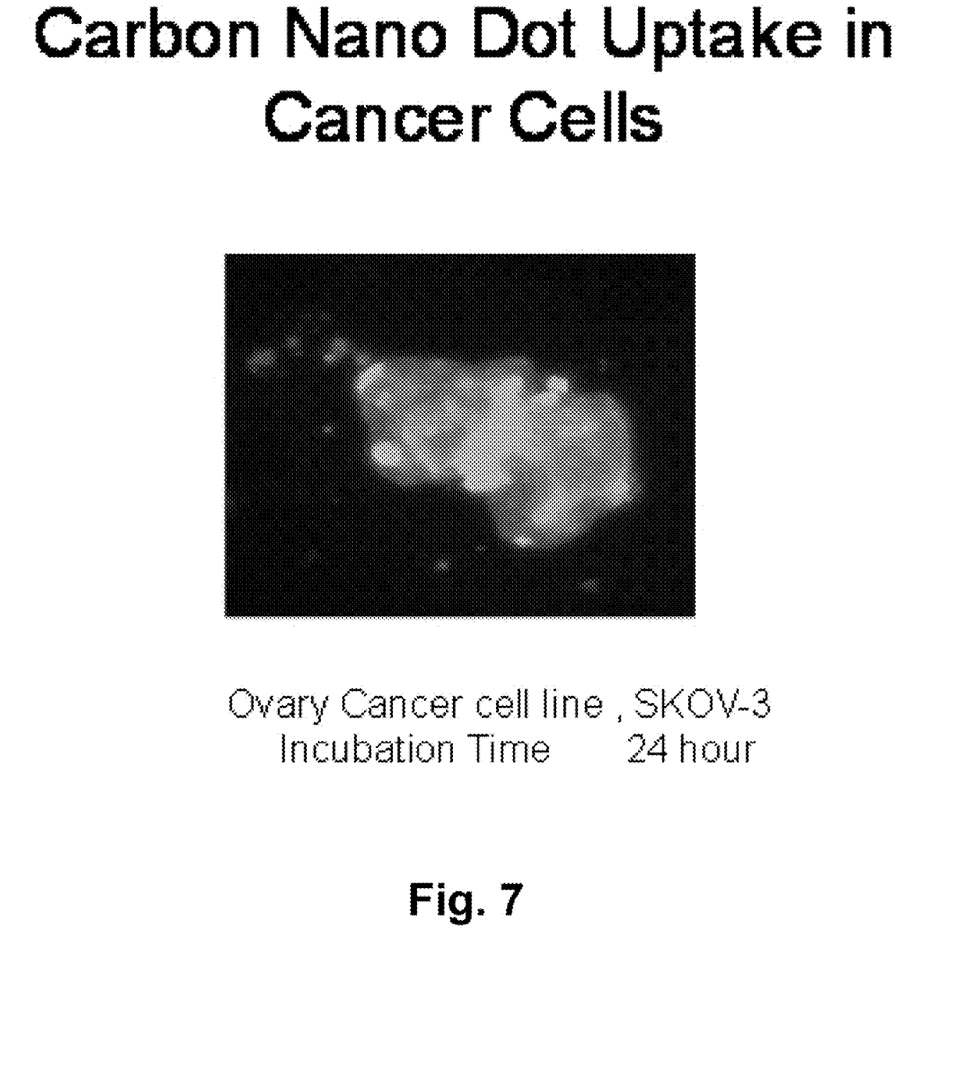
FIG. 7 is fluorescence imaging of the uptake (24 hrs) of C-dots by ovarian cancer cell line (SKOV-3).

In FIG. 7 the image of an ovarian cell line by C-dot is shown. The incubation time of the C-dot was 24 hr.

Examples and the explanations herein are intended to be illustrative of the present invention and not to be construed as limiting in any manner. The invention is defined by the following claims with equivalents to each claim and part of the claim intended to be included therein.

What is claimed is:

1. A water soluble self-fluorescing quantum carbon dot comprising a carbon dot isolated from carbon soot and treated to produce hydrophilic carboxylic acid groups on the surface of the carbon dot sufficient to cause fluorescence.

2. A composition according to claim 1 which has been bonded to a desired molecule as a fluorescent tag.

3. A composition according to claim 2 wherein the molecule is a part of a bacteria such that the bacteria become tagged.

4. A composition according to claim 2 wherein the molecule is used to tag a cancerous ovary cell line as a fluorescent tag.

5. A composition according to claim 1 wherein the carbon dots have a size of from about 2 nm to about 7 nm.

6. A composition according to claim 1 wherein the carbon dots have been treated by oxidative means to produce hydrophilic carboxylic acid groups on the carbon dot.

7. A composition according to claim 1 wherein the carboxylic acid groups are covalently attached to the surface of the carbon dot without the use of polymeric materials wrapping the carbon dot.

8. A composition according to claim 1 wherein the carbon soot is from a hydrocarbon wax.

9. A method of producing a fluorescent quantum carbon dot comprising
   a. heating a hydrocarbon wax to a temperature of between about 500 degree C. and 800 degrees C. under conditions sufficient to produce carbon soot;
   b. collecting and purifying the soot to isolate quantum carbon dots;
   c. oxidatively treating the quantum carbon dots to remove amorphous carbon and produce hydrophilic carboxylic acid groups on the surface of the dots sufficient to cause the dots to fluoresce.

10. A method according to claim 9 wherein the oxidative treatment is with nitric acid.

11. A method according to claim 9 wherein the purifying is accomplished by solvent washing followed by filtration.

12. A method of tagging a molecule or biological system comprising associating a water soluble self-fluorescing quantum carbon dot with the molecule or biological system.

13. A self-fluorescing hydrocarbon quantum carbon dot functionalized with carboxylic acid groups on the surface of each dot sufficient to cause fluorescence.

* * * * *